United States Patent [19]

Ringle et al.

[11] Patent Number: 5,183,063
[45] Date of Patent: Feb. 2, 1993

[54] DENTAL FLOSS AND PRE-THREADED LEADER

[75] Inventors: Larry L. Ringle, 645-2 Woodside Sierra, Sacramento, Calif. 95825; Ronald G. Lax, Grass Valley, Calif.

[73] Assignee: Larry Lee Ringle, Sacramento, Calif.

[21] Appl. No.: 712,405

[22] Filed: Jun. 10, 1991

[51] Int. Cl.⁵ ............................................. A61C 15/00
[52] U.S. Cl. ...................................... 132/321; 132/329
[58] Field of Search ............... 132/321, 323, 327, 329; 433/2, 3; 223/99, 102

[56] References Cited

U.S. PATENT DOCUMENTS

| | | | |
|---|---|---|---|
| 1,801,691 | 4/1931 | Ripper | 223/102 |
| 2,721,014 | 10/1955 | Allen | 223/102 |
| 3,160,157 | 12/1964 | Chisman | 223/102 |
| 3,650,392 | 3/1972 | Haagedourn | 132/324 |
| 3,929,144 | 12/1975 | Tarrson et al. | 132/323 |
| 4,080,777 | 3/1978 | Griset, Jr. | 57/140 J |
| 4,790,254 | 12/1988 | Vornholt | 223/102 |
| 4,832,063 | 5/1989 | Smole | 132/329 |
| 5,050,625 | 9/1991 | Siekman | 132/323 |

Primary Examiner—Gene Mancene
Assistant Examiner—Frank A. LaViola
Attorney, Agent, or Firm—Bernhard Kreten

[57] ABSTRACT

An integrally formed dental floss and leader which lends itseld to oral prophylaxis especially for implants and bridges. The floss is captured by the leader through a hinged door which swings from an open to a closed position during fabrication to provide an integral unit for use by a floss user.

23 Claims, 4 Drawing Sheets

DENTAL FLOSS AND PRE-THREADED LEADER

FIELD OF THE INVENTION

The following invention relates generally to an improved form of dental floss having exceptional plaque-removing capabilities and a leader coupled thereto. More particularly, the invention relates to multi-ply acrylic fiber which has an excellent ability to remove plaque and a leader of the type which lends itself for use with dental bridges and implants. A leader is formed on one free end of the acrylic fiber to facilitate placement of the floss in plaque-collecting areas.

CROSS REFERENCE TO RELATED APPLICATION

This application reflects ongoing research in dental floss technology, variants of which were shown in Ser. No. 07/307,634, filed Feb. 8, 1989, by the present inventor.

BACKGROUND OF THE INVENTION

Since the mid-1960's plaque has been identified as playing at least a major role in causing dental problems both with respect to caries and periodontal disease. However, the actual mechanism by which plaque operates is still subject to conjecture. Plaque, a film of mucus which is produced in the mouth, is a known medium which can harbor bacteria both on the tooth and adjacent gum tissue. It is now generally recognized that removal of plaque is essential for promulgating oral hygiene.

Although substantial research and product engineering has occurred over the last 25 years with a view towards effectively removing plaque, certain difficulties still exist. The following prior art describes the on going efforts of others attempting to solve this long standing problem which has yet evaded solution, and these prior art citations are included to discharge applicant's acknowledged duty to disclose prior art with which he is familiar:

| INVENTOR | PATENT NO. | ISSUE DATE |
|---|---|---|
| Cowardin, C. M. | 119,745 | October 10, 1871 |
| Ripper | 1,801,691 | April 21, 1931 |
| Stonehill | 2,381,142 | August 7, 1945 |
| Footer, J. | 2,612,177 | September 30, 1952 |
| Graham | 2,620,104 | December 2, 1952 |
| Petitta, M. | 2,931,371 | April 5, 1960 |
| Hendy | 3,525,460 | August 25, 1970 |
| Doiron | 3,531,030 | September 29, 1970 |
| Haagedoorn | 3,650,392 | March 21, 1972 |
| Wells, R. L. | 3,744,499 | July 10, 1973 |
| Thornton | 3,837,351 | September 24, 1974 |
| Standish et al. | 3,838,702 | October 1, 1974 |
| Hardwick | 3,880,167 | April 29, 1975 |
| Thornton | 3,896,824 | July 29, 1975 |
| Wells, R. L. | 3,930,059 | December 30, 1975 |
| Pace | 3,987,839 | October 26, 1976 |
| Tarrson et al. | 4,011,658 | March 15, 1977 |
| Guyton, W. C. | 4,029,113 | June 14, 1977 |
| Oldham, G. R. | 4,064,883 | December 27, 1977 |
| Negishi, et al | 4,070,815 | January 31, 1978 |
| Griset, Jr. | 4,080,777 | March 28, 1978 |
| Naslund | 4,133,339 | January 9, 1979 |
| Griset, Jr. | 4,155,216 | May 22, 1979 |
| Griset, Jr. | 4,159,619 | July 3, 1979 |
| Perri, S. | 4,182,341 | January 8, 1980 |
| Griset, Jr. | 4,184,316 | January 22, 1980 |
| Thomas et al | 4,215,478 | August 5, 1980 |
| Eaton, II | 4,265,258 | May 5, 1981 |
| Russell | 4,274,565 | June 23, 1981 |

-continued

| INVENTOR | PATENT NO. | ISSUE DATE |
|---|---|---|
| Weber | 4,385,575 | May 31, 1983 |
| Paudler | 4,441,497 | April 10, 1984 |
| Donovan, M. | 4,523,600 | June 18, 1985 |
| Finkelstein et al | 4,583,564 | April 22, 1986 |
| Feuerman | 4,667,860 | May 26, 1987 |
| Smole, F. T. | 4,832,063 | May 23, 1989 |

Generally, the techniques for plaque removal are predicated on two principles. The first involves plaque removal through "washing" the plaque from the mouth area by means of liquids. Second, plaque removal has been attempted by mechanical brushing.

With respect to washing, certain mouthwashes are commercially marketed without prescription which purport to be effective in plaque control. These however are not registered with the Food and Drug Administration, and are listed merely as cosmetics. Available research data suggests that these mouthwashes are less than completely effective. A second known liquid, Peridex, is available under prescription and is a known plaque-removing liquid, but is objectionable to the extent that side effects are exhibited in some individuals. These side effects include adverse teeth staining and affection one's taste perception. Even with an effective liquid, the film-like quality of plaque thwarts highly efficient removal through mere mouthwashing, and is singularly ineffective when trying to remove plaque in the sulcus area of one's mouth, i.e., the narrow trough-like gap between one's tooth and the gum tissue. This is also critical interproximally (in between the teeth) since this is where most periodontal disease and caries occur. When a patient, already afflicted by periodontal disease or for other reasons, uses dental implants, bridges or has had subgingival curettage or surgery performed, interproximal spaces greater than 4 mm exist between teeth and or adjacent the sulcus. This provides greater opportunity for further plaque formation and gum disease.

To a certain extent, plaque formation is not a problem on tooth surfaces that can receive direct mechanical contact with an instrument such as a brush which effectively breaks up the plaque film and therefore allows the plaque and its associated entrained bacteria to be carried away. Many brush manufacturers claim their bristles will go below the gum (in the sulcus) on the buccal and lingual—but not interproximally. Thus, along those areas where direct brush contact is possible, plaque buildup is less of a problem. However, brushes still are quite ineffective in removing plaque both along the area immediately below the gum line, i.e., the sulcus and interproximally. The problem is exacerbated when patients have had periodontal related dental procedures performed.

As knowledge with respect to the role that plaque plays in dental disease has grown, so too had the change in the design of various types of dental floss. While dental floss was once used substantially as a toothpick for the removal of entrained matter caught between teeth, various changes in dental floss appearance, particularly in the last few years reflect the belief that dental floss can be used to remove plaque in areas normally inaccessible by any other means particularly especially when the floss is used daily. Most designs involve contouring the external configuration of nylon or polyethylene to form an abrasive surface which can break up the plaque film under the gum line and between teeth to solve the problem. Earlier attempts have included the use of fibers formed from silk, cotton, nylon or blends thereof.

All of these known prior art flossing structures are less than desirable in that they are either too abrasive which adversely effects the enamel on the tooth, are too sharp which can cause damage to the gum tissue by cutting the gums, or are ineffective in removing the plaque. Moreover, taking this floss under the gum actually causes pain and the patient, therefore, will not take floss under the gum to remove plaque in the normal 3 mm sulci.

Another problem involves the geometry of prior art leaders themselves. Commercially available threaders for use with bridges, implants, etc. must first be threaded with the floss because they do not come pre-threaded. This can be inconvenient and discouraging to a prospective user. Further the geometry of many threaders make their use further frustrating. Among other things, saliva makes the threader too slippery to use.

Another problem is that extremely small threaders may impose a point load on the floss which makes fracture of the floss likely. When this occurs, the floss is entrained in the person's mouth and can be difficult to remove.

Another problem is that small threaders—typically formed by injection molding—are difficult to make without inducing zones of weakness in the threader. Plastic, such as nylon when unstressed or ideally formed, exhibits long molecular chains for greatest tensile strength. "Hairpin" turns (such as adjacent a threaded eyelet) tend to shorten the molecular chain inducing failure of the threader itself upon tensile loading by the floss.

Other threaders utilize a seam at the hairpin turn which is a natural area of weakness and therefore failure.

SUMMARY OF THE INVENTION

The instant invention is distinguished over the known prior art in that the inventor has discovered that acrylic fiber advantageously removes unwanted plaque yet does so without damaging either the tooth's enamel or gum's tissue. While the exact reasons why acrylic fiber are superior to known prior art materials may be the basis of some speculation and conjecture, the inventor's extensive "split-mouth" studies, comparing the known prior art to acrylic fiber demonstrates efficacy.

One primary reason appears to be the denure or "fuzziness" of the acrylic fiber when it is configured as floss like substance. The acrylic fiber exhibits a plurality of outwardly extending free ends which appear well suited to reach within the bottom most area of the sulcus and gently remove plaque therefrom. It is to be noted that in a healthy mouth, the depth of the trough defining the sulcus is approximately 3 mm interproximally. Plaque is manufactured by the body and forms in this trough area. Since plaque consists of bacteria, "fresh" plaque (i.e., less than 24-36 hours) is not believed to be harmful because it does not contain a high number of pathogenic bacteria. When the plaque becomes old, however, the bacteria present will attack the tooth and tissue area against which it abuts, causing periodontal disease. Regular use of floss formed from acrylic fiber stops the infection.

A second advantage attributable to the use of acrylic fiber as a dental floss involves the coefficient of friction associated with the acrylic fiber when it is configured as a floss like substance. Because the mechanical flossing motion is oscillatory, back and forth along the length of the floss strand, friction is generated and dissipated in the form of heat when using acrylic fiber as a floss. This provides a thermal sensor to the user of the floss as to the relative vigor with which the flossing should be conducted for best results. Unlike prior art fibers used in flossing which have coefficients of friction different from acrylic fiber, and therefore result in either too vigorous or too light a flossing motion, acrylic fiber's coefficient of friction appears to correlate with effective flossing technique.

A third possible reason for the enhanced benefits associated with acrylic fiber according to the instant invention devolves from gingival stimulation and not inflammation as can occur with some prior art devices. The cross-sectional diameter of the floss formed from the acrylic fiber according to the present invention is kept within certain ranges depending upon the characteristics of the flosser's mouth. Factors include the relationship of one's gums to the teeth, the interproximal gap between adjacent teeth and the depth of pockets with the sulcus. For individuals who have had periodontal surgery, plural strands of plural-ply acrylic fiber have been found to be an effective hygienic apparatus. Dental implants involve the use of support posts which elevate the implanted teeth above the gum. This provides a space which is inaccessible by normal flossing unless a leader is used.

A fourth known reason involves the beneficial characteristics of acrylic fiber as a flossing tool. The acrylic fiber appears to have the requisite absorbency to actually serve as a carrier in removing unwanted plaque. Thus, whereas the fibers initially served to break up the film placed on the teeth and gums of the flosser, the fibers also absorb the plaque and remove it from the site of potential harm. The floss thus buffs the plaque off.

A fifth reason involves the disturbance of existing sites of necrosis and festering inflammation. When the floss is used regularly, objectionable odors associated with halitosis abate as a function of time.

Viewed in its essence, the instant invention is directed to dental floss formed from acrylic fiber integrally coupled to a specially formed leader. The floss may be formed from braiding a plurality of acrylic fiber strands, and in one form of the invention, sets of braided strands are disposed in stacked registry and used simultaneously to occupy as much of a gap as exists between adjacent teeth, underlying support tissue and supporting implant posts.

The leader itself works most efficiently when it is of relatively small dimension (compared to the floss cross-section when unstressed) and is somewhat textured. It does not exhibit the same characteristics as the floss (which is intended to contact and remove the plaque) but rather is formed from different material, such as plastic. Consequently, the leader is characterized in its relatively small cross-sectional diameter when compared with the floss and has a substantially lower coefficient of friction than the floss. Thus, the leader can pass between the implant posts, gum and bridgework. The floss itself is then pulled between spaces of the dental appliance.

Striking a balance between forming a leader which does not harm the user's teeth, gums or bridgework and is yet easily graspable is one hallmark of the instant invention. Saliva on plastic renders most leaders hopelessly slippery.

Another hallmark of the instant invention involves the minimal failure rate of the leader and floss at the point of greatest stress—at the trailing end of the leader where the floss contacts the leader.

The essential feature is to attach an extremely small leader in such a way that the floss can be used in relatively tight clearances with minimal dexterity requirements imposed upon the user. Another hallmark of the instant invention is it's ability to be used within the minimal clearances indigenous with the flossing operation and by individuals having relatively modest dexterity skills to increase the likelihood that the user will not be dissuaded from practicing good oral hygiene techniques. It should be noted that any program of oral prophylaxis is predicated on habitual hygienic practices. One characteristic of the instant invention is that it removes many frustrations that attend prior art flossing structure and techniques such as threading the leader and leader failure. Increasing the likelihood that the device will be used on a regular basis with a minimal amount of disruption reinforces pre-existing good dental habits and encourages good new habits.

OBJECTS OF THE INVENTION

Accordingly, it is a primary object of the present invention to provide a new and useful dental flossing implement.

A further object of the present invention is to provide a device as characterized above which is relatively inexpensive to manufacture, benefits from mass production techniques, and is durable and safe to use.

A further object of the present invention is to provide a device as characterized above which efficiently removes plaque from areas not as accessible by known prior art instrumentalities.

A further object of the present invention is to provide a device as characterized above in which the floss has a co-efficient of friction such that the flosser has readily discernable feedback which correlates with the quantum of pressure for efficient use of the floss. The leader is readily graspable yet does not adversely affect one's teeth, gums and dental appliances.

A further object of the present invention is to provide a device as characterized above which can be used as a post-surgical prophylactic and with implant anchored or supported dentures or bridges, as well as standard fixed bridges.

A further object of the present invention is to provide a device as characterized above which includes a plurality of fibrous free ends which can extend into the trough-like recess that exists between supporting tooth tissue and the teeth to not only remove plaque but also stimulate the gingiva.

A further object of the present invention is to provide a device for flossing dental appliances such as bridges, implants and the like which includes a leader having a free end and a tethered end, the tethered end including a door and acrylic fiber floss connected to said tethered end via the door such that, during fabrication of the device, the floss is looped about a hinge of the door and the door is shut.

A further object of the present invention is to provide a device as characterized above which includes integrally formed dental floss and leader for use with bridges, implants or the like, the leader has a free end for threading into interproximal dental spaces and a tethered end which supports said floss, the tethered end including the floss precaptured thereto.

Viewed from one vantage point, it is an object of the present invention to provide an instrumentality which is formed from a leader connected to an elongate strand of acrylic fiber material having a plurality of outwardly extending fibrous free ends which contact plaque and remove the plaque from the surface of a tooth, dental appliance and an adjacent sulcus between the tooth, the appliance and its surround gum tissue.

Viewed from a second vantage point, it is an object of the present invention to provide dental floss formed from a strand of acrylic fiber having an uncompressed cross-sectional diameter greater than and a compressed cross-sectional diameter less than the spacing between teeth, gums and dental appliances, and a leader extending from an end of the acrylic fiber strand having a cross-sectional diameter which promulgates threading between the appliance and the gum or other teeth.

Viewed from yet a third vantage point, it is an object of the present invention to provide a method for forming dental floss which includes connecting a strand of acrylic fiber to a leader for inserting the fiber between a dental appliance and other dental areas in one's mouth.

Viewed from yet a fourth vantage point, it is an object of the present invention to provide a method for forming a flossing device for cleaning interproximal dental spaces like spaces existing between dental bridges, implants or the like and other dental structures such as teeth and gums, forming a leader with a door having a hinge and looping a floss about the hinge of the leader door and sealing the door shut on the floss. This method can thus precapture any flossing material, such as nylon, cotton, wool, etc., acrylic fiber however, being preferred.

These and other objects will be made manifest when considering the following detailed specification when taken in conjunction with the appended drawing figures.

DESCRIPTION OF THE DRAWINGS FIGURES

FIG. 11 A is a view of an alernate energy absorber arrangement.

FIG. 11 B is a view of another alternate energy absorber arrangement.

DESCRIPTION OF PREFERRED EMBODIMENTS

Considering the drawings now, wherein like reference numerals denote like parts throughout the various drawing figures, reference numeral 10 is directed to a leader according to one form of the present invention, reference numeral 30 is directed to a second form of leader according to the present invention and reference numeral 50 is directed to the acrylic fiber floss which forms a part of the invention.

In essence, both leaders include a free end, a central arcuate body, and a linear trailing portion. In turn, the linear trailing portion communicates with a door-like structure which captures the acrylic floss therewithin. The area of juncture between the floss and the door is such that internal stresses in the leader have been minimized to prevent fracture under tensile load and the interface between the floss and the door induces minimal stress on the acrylic floss 50.

Figure 1:
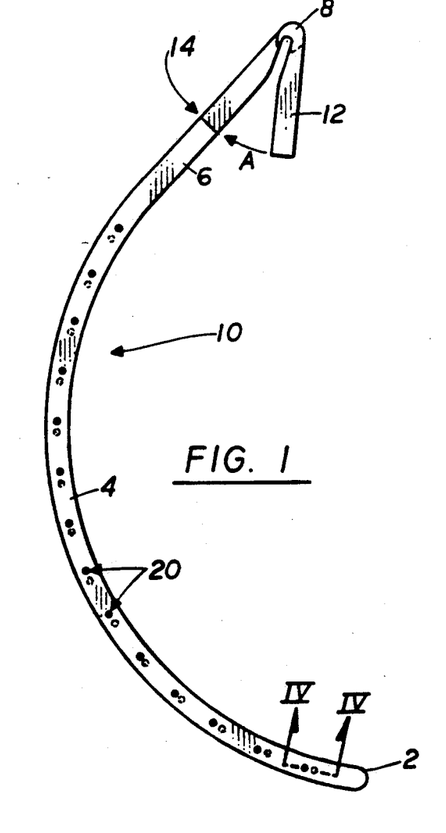
FIG. 1 is a left side view of a first embodiment of the threaded leader.
Figure 2:
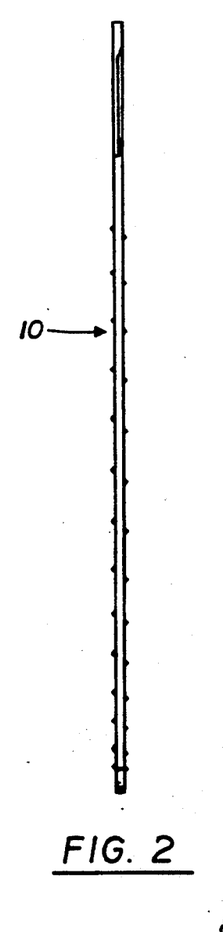
FIG. 2 is a front view thereof.
Figure 3:
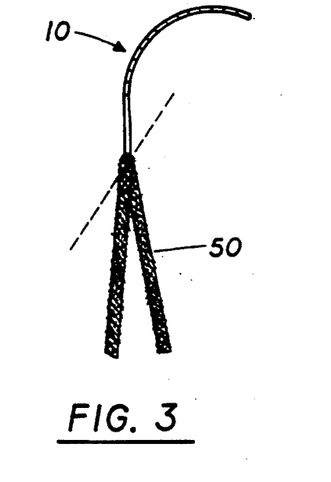
FIG. 3 is a right side view with floss.
Figures 4, 5:
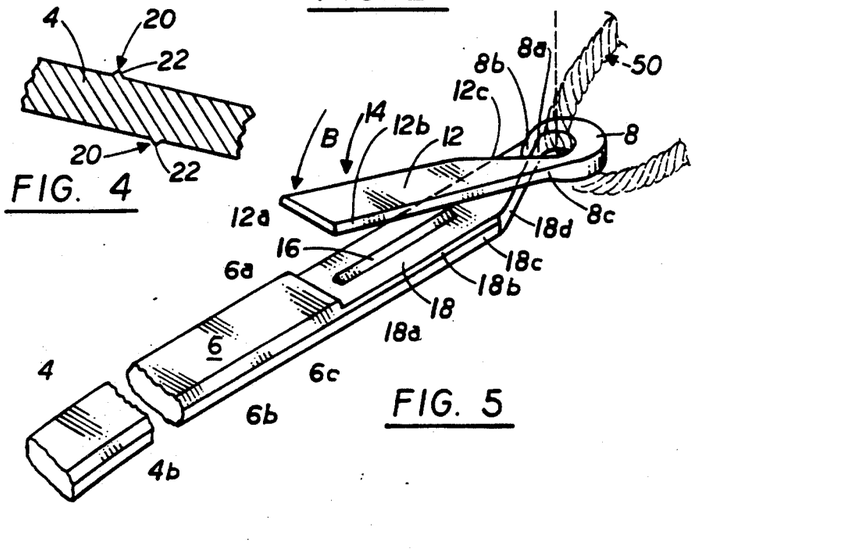
FIG. 4 is a sectional view along live IV—IV of FIG. 1.
FIG. 5 is an enlarged area of a tethered portion of the leader with floss.

More particularly, and with reference to FIGS. 1 through 5, the first leader 10 is operatively coupled to the acrylic floss 50 and includes the following structure. In essence, a free end 2 of the leader 10 is provided with a radiused leading portion i.e., absent any sharp projection. The leader continues rearwardly to an arcuate central body 4. A linear trailing portion 6 communicates with the arcuate central body 4 and leads to the door structure. As shown in FIGS. 2 and 4, a plurality of tactile enhancement means 20 are provided on opposed flat surfaces of the central body 4. As shown especially in FIG. 4, these tactile enhancement means 20 may take the form of pointed projections 22 on opposite flat sides of the central body 4. Note that these projections are offset slightly one from the other.

With respect to FIG. 5, it is there shown that the trailing portion 6 includes a jamb 6a immediately adjacent to a door 12 to be defined infra. Also, the linear trailing portion 6 has side edges provided with an upper chamfer 6b and a lower chamfer 6c such that sharp edges along junctures between top and side faces have been minimized. Alternatively, these side edges could be radiused for similar benefits. As shown, the arcuate body portion 4 also includes an upper chamfer 4b and a lower chamfer 4c. The juncture 14 where the leader and floss intersect can now be explored according to the first embodiment.

In essence, a trailing portion of the leader includes a boss 8 having a substantially constant radius of curvature and an interior hole 8a through which the acrylic floss 50 passes. The transition between the hole 8a and a top and bottom surface of the boss 8 can be radiused to minimize sharp edges which may induce floss fracture. Between the linear trailing portion 6 and the boss 8, a lower portion of the leader-floss juncture 14 includes a support 18 and the door 12.

The support 18 includes a top surface upon which a raised bead 16 is supported. The raised bead 16 is polygonal in shape and may have a triangular cross-section. The bead's length runs parallel to the long axis of the support 18. The raised bead 16 can be made from the same material as the rest of the leader and is intended to be dispersed under focused sonic radiation to provide a seal by melting the bead along the juncture between the bead support 18 and the door 12 to be explained further.

The bead support 18 includes a doorstop 18a which is tantamount to a step or transition between the linear trailing support 6 and the planar top surface of the bead support 18. Stop 18a is adapted to receive a leading edge 12a of the door 12 thereagainst. The bead support 18 includes an upper chamfer 18b and a lower chamfer 18c similar to that which was discussed for both the linear trailing portion 6 and the central arcuate body 4. However, the upper chamfer 18b has been abbreviated so that when the door is sealed thereagainst, a continuum will have been provided in association with a shoulder 12b of the door provided with and following the upper chamfer 6b and 18b.

The bead support 18 adjacent the boss 8 includes a taper 18d providing communication between the boss 8 and the bead support 18. The taper 18d provides a smooth narrowing to allow clearance for the floss 50 to pass through the boss hole 8a. A ramp 8b ascends from the area of transition from the bead support 18 to the boss 8. The boss 8, at its distal extremity remote from the linear portion 6 has a thickness substantially that of the linear trailing portion 6. Thus, the ascending ramp 8b of the boss goes from a thickness slightly greater than half of the leader to the full thickness of the leader at the boss.

As the boss 8 extends towards and is integrally formed with the door 12, a further descending ramp 8c is provided along a lateral extremity of the boss 8 as it transitions to the door 12. Similarly, the door 12 includes a taper 12c which follows descending ramp 8c of the boss so that the top surface of the door 12 is substantially smooth and flat similar to the linear trailing portion 6.

When the leader has been manufactured, preferably by injection molding techniques, the unstressed, at rest position is shown in FIG. 1. Next, it is desired to loop the acrylic floss 50 into the hole 8a of the boss 8 which is easily accomplished since the door 12 is offset from the long axis of the leader as defined by the trailing linear portion 6 and the bead support 18. Rotation of the door in the direction of arrow A of FIG. 1 produces the orientation of FIG. 5 for the next step.

The acrylic floss 50, positioned as in FIG. 5 then allows the door to be moved to its second position as indicated by the arrow B of FIG. 5 to effect tangential registry between the door 12 the bead support 18 and leading edge 12a of the door 12 and door jamb 6a. When thus positioned as suggested by FIG. 2, a focused source of sonic radiation directed at the raised bead 16 will cause migration of the material defining the raised bead along the interface between the door 12, support 18 and environs to secure final adhesion for the finished product.

The raised bead is shown as oriented parallel to the long axis of the bead support and trailing linear portion 6 and centrally located so that dispersion of the material defining the raised bead produces a reliable seal with minimal "flash" i.e., excess material migrating onto the exterior surfaces of the leader floss juncture 14. It should be noted that the door 12 includes a chamfer 12b which follows the upper chamfer 6b and 18b to facilitate this smooth transition, and the door leading edge 12a complements the jamb 6a of the linear trailing portion to provide a substantially seamless structure.

It is also possible to configure the interfit between the jamb 6a and the door leading edge 12a such that a friction-fit will have been evidenced thereat which may be supplemented by the ultrasonic welding or other form of radiant, thermal, chemical or adhesive bonding. Alternatively, the linear portion's jamb 6a could be tapered to provide a projection (not shown) with a complemental projection on the door leading edge 12a to provide a locking snap fit. However, these types of undercuts do not lend themselves as readily to injection molding elegance.

The relevant portion detailed thus far results in a device shown in FIG. 3 which resolves nettlesome problems which heretofore existed in known structure. More specifically, this device defines a leader which is prethreaded to the floss unlike prior art devices and provides an extremely durable construction less prone to failure than was evidenced in the prior art. By providing the boss 8 with an arcuate contour of substantial thickness, this former site of failure will have been avoided. Also by providing the boss hole 8a as shown and described hereinabove, the load imposed upon the acrylic floss will have been minimized and relatively free from undesirable sharp edges which were heretofore sites of weakness.

Most of the drawing figures remaining, i.e., FIGS. 6 through 16 reflect a second embodiment of a leader 30 in many ways similar to the first discussed embodiment with a few notable exceptions. One exception involved the orientation of the acrylic floss 50 with respect to the leader. For example, FIG. 5 reflects that the longitudinal axis of the acrylic floss 50 is perpendicular (axis Y) to the top and bottom planar surfaces of the leader, for example as shown by reference numerals 6 and 12 of FIG. 5. By way of contrast, and with respect to FIGS. 15 and 16, the acrylic floss 50 is oriented parallel to the major planar surfaces of the second embodiment. This is exemplified by the axis Z.

Certain advantages attend this second embodiment. For one thing, the entire width of the leader can be used to sandwich the acrylic floss therebetween. This has significance when one considers that it is the thickness of the leader which is a limiting parameter in dimensional design of the leader since it is the thickness of the leader which must pass between adjacent teeth e.g. so that this clearance i.e., the thickness can be critical in many environments. Conversely, the width of the leader is not so critical a design feature.

Another apparent difference between the two embodiments is that the motion required for closing the door 42 of the second embodiment requires only rotational movement about the hinge of the leader whereas in the first embodiment, rotation of the door about two different directions was required. Thus, a prethreaded floss is more easily manufactured according to the second embodiment because only one axis of rotation will have been required.

Figures 6, 7, 8, 9, 10, 11:
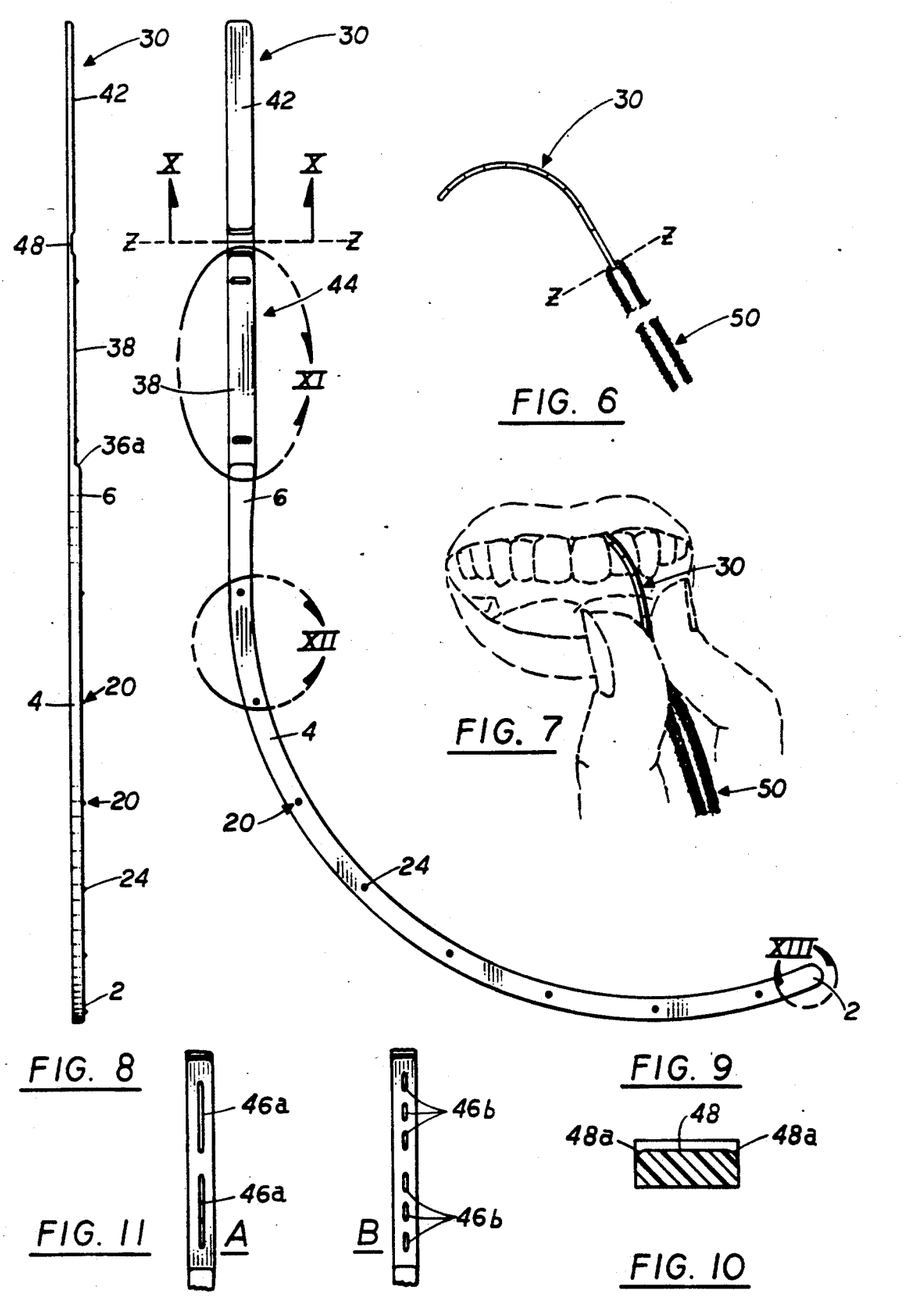
FIG. 6 is a view of a second embodiment.
FIG. 7 is a view of the second embodiment in use.
FIG. 8 is a front view thereof.
FIG. 9 is a right side view thereof.
FIG. 10 is a sectional view along line X—X of FIG. 9.
Figures 13, 14:
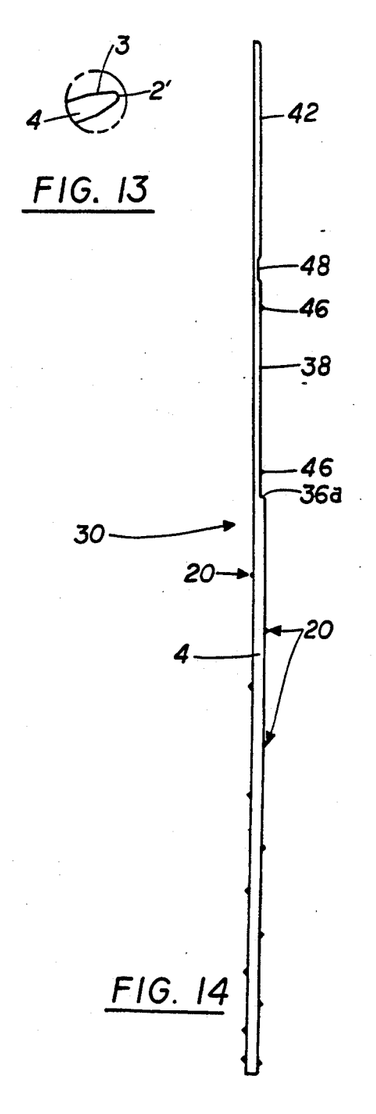
FIG. 13 is a detailed view showing an alternate tip.
FIG. 14 is a front view similar to that which is shown in FIG. 8.
Figure 15:
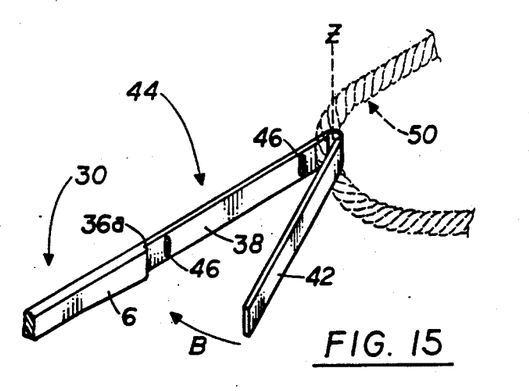
FIG. 15 is an enlarged view showing yarn about to be entrapped.
Figure 16:
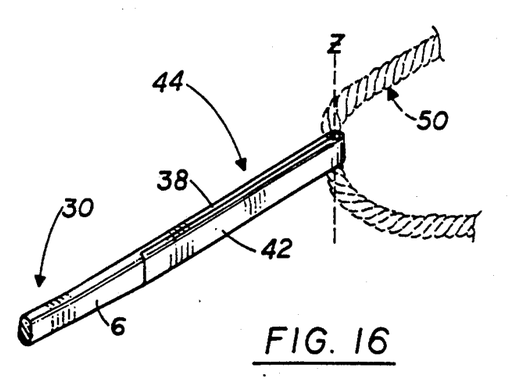
FIG. 16 is an enlarged view showing yarn having been entrapped.

More specifically, the leader 30 includes a free end 2 which, as shown in FIG. 9, has been radiused similar to the previous embodiment. However, consideration of FIG. 13 shows that the free end 2' shows a radius but an interposed taper 3 has been provided between the radius and the arcuate body portion 4. This taper 3 can facilitate the threading of the leader 30 between spaces in a persons mouth. The FIG. 13 structure is equally amenable to the first embodiment.

The arcuate central body 4 is substantially similar to the first embodiment but a variant with respect to the tactile enhancement means 20 is reflected. Although pointed projections or protuberances 22 have been described with respect to the first embodiment, hemispherical projections or protuberances 24 could be utilized as suggested in FIGS. 8 and 9. Also, unlike FIG. 2, these projections or protuberances 24 are only found on one planar surface of the arcuate portion 4. An alternative, shown in FIG. 14 reflects either the pointed projections 22 or the hemispherical projections 24 on both sides of the arcuate body portion 4 and instead of a slight offset, one from the other on opposite sides of the arcuate portion 4, the offset is such that a projection 20 on one side is equi-spaced from two projections on an opposite side.

Figure 12A:
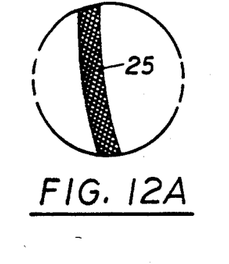
FIGS. 12A-D are views of alternate ribbing styles.
Figure 12B:
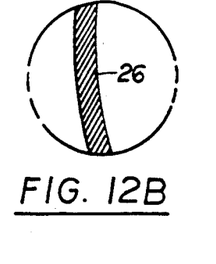
Figure 12C:
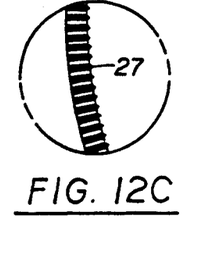
Figure 12D:
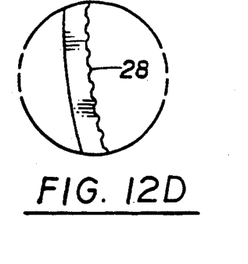

FIGS. 12A, B, C, and D show further variance of tactile enhancement means 20. For example, FIG. 12A reflects that the planar surface on the arcuate portion 4 could be knurled 25. This knurling occurs in two directions orthogonally disposed relative to each other. FIG. 12B reflects another form of knurling 26 in which the texturing has been applied only in one direction in general at a 45° angle with respect to a transverse section. FIG. 12C teaches the use a plurality of cleats 27 running transverse to the length to the arcuate body portion providing a crenelated effect along a major planar surface thereof. FIG. 12D shows another type of crenellation with a serpentine border 28 being provided along one edge of the leader at the juncture of a side wall with a top wall.

Because the floss 50 is captured by the leader along the Z axis parallel to the major planar surfaces of the leader, the width of the leader can be substantially less than the width of the first embodiment. This is because sufficient material had to have been placed around the area where the floss 50 is captured by the boss 8 and which defines a hinge for the door 12. Another difference is that it is not necessary to provide a chamfer on the side walls of the leader. Thus, the linear portion 6 of FIGS. 15 and 16 do not reflect a chamfer.

Another salient difference between the two embodiments is shown where the door jamb 36a is provided at the transition between the linear portion 6 and the support base 38 upon which the ultrasonic beads 46 are disposed. As reflected in the drawings, the jamb 36a can be radiused at the transition between the linear portion 6 and the support 38. The support 38 has a top surface upon which the raised beads 46 are supported. These beads 46 are shown as transverse to the long axis of the linear portion of the leader. This variant could be also provided in the first embodiment and vice versa. Also, as in the first embodiment, these beads may be formed as prisms having substantially triangular cross-section. FIGS. 11A and 11B reflect other bead orientations that have efficacy. FIG. 11A shows two beads linearly oriented parallel to the long axis of the tethered portion 14 of the leader. FIG. 11B shows two sets of three beads similarly oriented.

FIGS. 8, 9 and 10 reflect certain hinge structure, the hinge shown as reference number 48. In general, the choice of plastic associated with the leader is such that a living hinge is provided by merely thinning the plastic at that area. Thus a sector of flexibility will have been provided allowing the door 42 to move from an open position (e.g. FIG. 8) to a closed position (e.g. FIG. 16). Besides being of lesser thickness than the major body portion of the leader, the hinge 48 also may include radiused edges 48a to provide stress relief for the floss 50 entrained thereon.

The other structural details of the door 42 and platform 38 may be structurally ornate (e.g., chamfered or radiused) as described with respect to the first embodiment or may be substantially unadorned as shown in the drawing figures.

Figure 17:
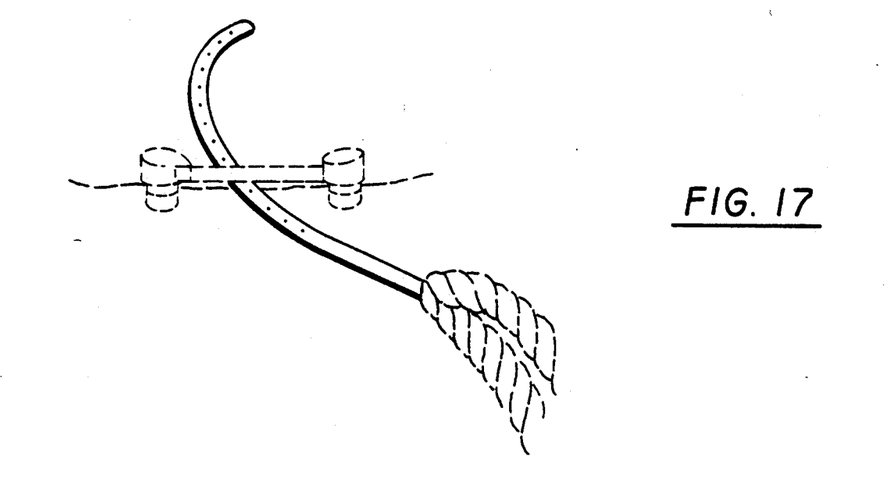
FIG. 17 shows the invention deployed in one manner.

FIG. 17 shows how the leader cooperates with a bar connected implant. The leader 10 or 30 is inserted between the implanted posts, below the transverse bar which co-joins the implanted posts. Flossing proceeds once the leader has been grasped and the floss contacts the bar and posts.

Figure 18:
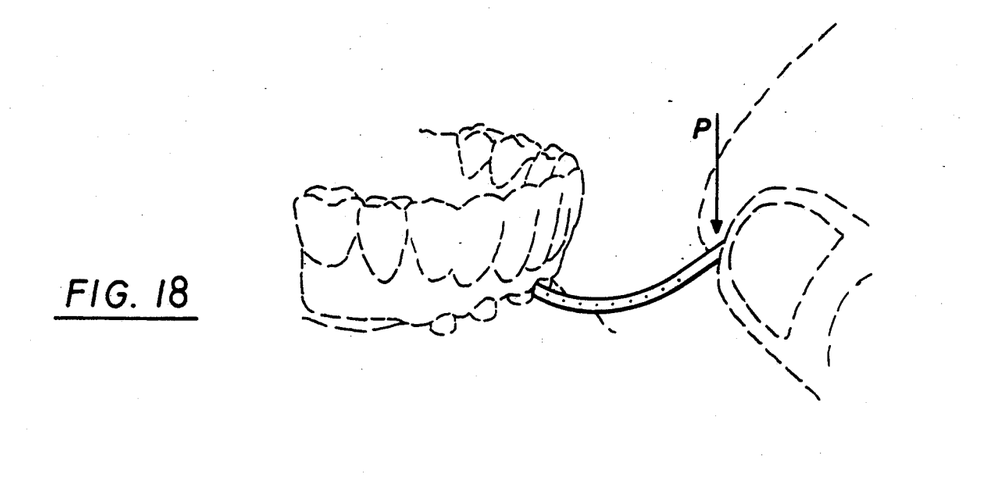
FIG. 18 shows the invention deployed in another manner.
Figure 19:
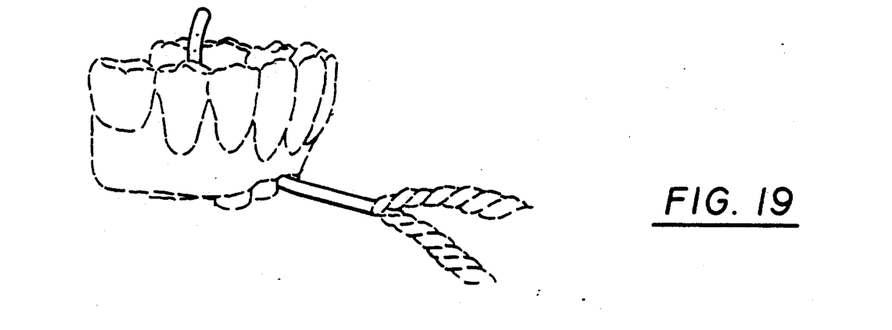
FIG. 19 shows the invention deployed in another manner.

FIGS. 18 and 19 show the technique for a fixed implant bridge where the leader is placed between posts and under the denture. The arcuate configuration of the leader allows the leading portion 2 to "pop up" (FIG. 19) when pressure (along arrow P, FIG. 18) is applied to the trailing end.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An integrally formed dental floss and leader for use with bridges, implants or other structures such as teeth and prosthodontic devices, comprising in combination:
    said leader having a free end for threading into interproximal dental spaces and a tethered end which supports said floss,
    said tethered end including means for fixedly prefusing said floss to said leader thereto in a manner preventing substantial sliding of said floss relative to said tethered end of said leader.

2. The device of claim 1 wherein said leader includes a tactile enhancement means on a body portion intermediate said free end and said tethered end for facilitating grasping and use of the said integral leader and floss, and wherein said leader maintains a substantially constant, low-profile cross-section such that said leader may pass entirely through any opening through which said free end of said leader may enter.

3. The device of claim 1 wherein said tethered end includes a support, a door and a hinge connecting said support to said door whereby said door swings from an open to a closed position with said floss interposed adjacent said hinge, and an adhesive interface is located between said door and said support, said support and said door being substantially planar along an interconnection interface, said interface also coplanar with a portion of said floss captured by said hinge.

4. The device of claim 3 wherein said support includes a raised bead on a base surface thereof adapted to be juxtaposed against said door, said bead being susceptible to radiation for devolution into an adhesive for sealing said door to said support.

5. The device of claim 4 wherein said hinge is embodied as a boss having a ramp communicating with said base surface at one end of said boss and another ramp communicating with said door at another end of said boss.

6. The device of claim 4 wherein said hinge is embodied as a thinned area between said support and said door defining a flexible hinge upon which said floss is supported.

7. The device of claim 4 wherein said tactile enhancement means is in the form of surface irregularities on an arcuate body portion interposed between said free end and said tethered end to assist in the grasping by one using the device.

8. The device of claim 7 wherein said hinge is in the form of a boss having a central opening passing therethrough which is transverse to a planar surface of said leader, and said floss passes through said hole in said boss.

9. The device of claim 8 wherein said boss includes first and second transitional areas, one said transitional area defining a taper and ramp which communicates with a base extending from said boss to an arcuate portion of said leader.

10. The device of claim 9 wherein said other transitional area of said boss includes a tapered ramp extending to said door.

11. The device of claim 7 wherein said hinge is formed from thin material on said leader and said floss is placed thereagainst and said door folds about an axis of said hinge which is parallel to a width of said leader.

12. The device of claim 11 where said hinge has radiused side edges against which said floss abuts for stress relief.

13. The device of claim 3 wherein ultrasonic means are interposed between said door and a base surface of said support for adhesion therebetween.

14. A method for forming a flossing device for cleaning interproximal dental spaces like spaces existing between dental bridges, implants or the like and other dental structures such as teeth and gums, the steps including:
    forming a leader with a door having a hinge,
    initially orienting the door in an open position,
    looping a floss about the hinge of the leader door,
    sealing the door shut on the floss in a manner securely capturing the floss to the leader.

15. The method of claim 14 including placing tactile enhancement means on a medial portion of said leader to assist in gripping said leader, said tactile enhancement means providing means to resist longitudinal slipping of the leader when grasped and moved by a hand of the user.

16. The method of claim 15 wherein said tactile enhancement means is evidenced by forming knurling thereon.

17. The method of claim 15 wherein said tactile enhancement means is formed by placing crenellations thereon.

18. The method of claim 15 wherein said tactile enhancement means is formed by placing protuberances thereon.

19. The method of claim 15 wherein said leader has a free end formed with an arcuate blunted leading tip portion.

20. A device for flossing dental appliances such as bridges, implants and the like, comprising in combination:
    a leader having a free end and a tethered end, said tethered end including a door, and
    acrylic fiber floss having a substantially uniform cross-sectional area along its length and having a plurality of outwardly extending fibrous free ends which contact and remove plaque from the dental environment, said floss connected to said tethered end via said door such that, during fabrication of said device, said floss is looped about a hinge of said door and said door is shut.

21. An integrally formed dental floss and leader for use with bridges, implants or other structures such as teeth and prosthodontic devices, comprising in combination:

said leader having a free end for threading into interproximal dental spaces and a tethered end which supports said floss, said tethered end including means for fixedly prefusing said floss to said leader in an orientation wherein said floss adjacent said leader remains in a plane coplanar with said leader, whereby both said floss and said leader can easily pass through a narrow interproximal space.

22. The device of claim 21 wherein a hinge of said leader adjacent said floss includes stress relieving means, whereby loads between said leader and said floss are more easily maintained.

23. The device of claim 22 wherein said stress relieving means are curved corners located between an inside surface of said leader and two opposing side surfaces of said leader.

* * * * *